US012636479B2

(12) United States Patent
Harding et al.

(10) Patent No.: US 12,636,479 B2
(45) Date of Patent: May 26, 2026

(54) VASCULAR ACCESS DEVICE AND RELATED SYSTEMS AND METHODS

(71) Applicant: Becton, Dickinson and Company, Franklin Lakes, NJ (US)

(72) Inventors: Weston F. Harding, Lehi, UT (US); Jonathan Karl Burkholz, Salt Lake City, UT (US); Curtis H. Blanchard, Riverton, UT (US); Megan Scherich, Salt Lake City, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 800 days.

(21) Appl. No.: 17/192,802

(22) Filed: Mar. 4, 2021

(65) Prior Publication Data

US 2021/0290264 A1 Sep. 23, 2021

Related U.S. Application Data

(60) Provisional application No. 62/993,685, filed on Mar. 23, 2020.

(51) Int. Cl.
*A61M 39/10* (2006.01)
*A61B 17/34* (2006.01)
(Continued)

(52) U.S. Cl.
CPC ......... *A61M 39/10* (2013.01); *A61B 17/3415* (2013.01); *A61B 17/3423* (2013.01);
(Continued)

(58) Field of Classification Search
CPC ............ A61B 17/3423; A61B 17/3415; A61B 2017/347; A61B 2017/3445; A61B 5/1433; A61B 5/1444; A61B 5/150175; A61B 5/15019; A61M 25/0113; A61M 25/0097; A61M 25/09041; A61M 2039/1077;
(Continued)

(56) References Cited

U.S. PATENT DOCUMENTS 9,186,100 B2 11/2015 Devgon
9,272,088 B2 3/2016 Bornhoft
(Continued)

FOREIGN PATENT DOCUMENTS

CN 203539776 U 4/2014
CN 108883225 A 11/2018
(Continued)

*Primary Examiner* — Darwin P Erezo
*Assistant Examiner* — Erin L Colello
(74) *Attorney, Agent, or Firm* — The Webb Law Firm

(57) ABSTRACT

A vascular access device may include a housing and an instrument disposed within the housing. The housing may include a proximal end, a distal end, a slot, and an advancement tab. The advancement tab may be configured to move linearly along the slot between a retracted position and an advanced position. A proximal end of the instrument may be coupled to the advancement tab such that, in response to the advancement tab moving from the retracted position to the advanced position, the distal tip of the instrument may be advanced beyond the distal end of the housing into a catheter assembly and/or vasculature of a patient.

18 Claims, 15 Drawing Sheets

(51) Int. Cl.

| | | |
|---|---|---|
| *A61M 25/00* | (2006.01) | |
| *A61M 25/01* | (2006.01) | |
| *A61M 25/06* | (2006.01) | |
| *A61M 25/09* | (2006.01) | |

(52) U.S. Cl.
CPC .... *A61M 25/0097* (2013.01); *A61M 25/0113* (2013.01); *A61B 2017/3445* (2013.01); *A61B 2017/347* (2013.01); *A61M 25/0606* (2013.01); *A61M 25/09041* (2013.01); *A61M 2039/1077* (2013.01)

(58) Field of Classification Search
CPC .... A61M 2005/323; A61M 2005/3247; A61M 2005/325; A61M 2005/3261; A61M 2005/3268; A61M 5/3257; A61M 5/326; A61M 5/3275; A61M 39/10; A61M 25/0606; A61M 25/0082; A61M 25/0021; A61M 25/00; A61M 2025/019
See application file for complete search history.

(56) References Cited

U.S. PATENT DOCUMENTS

| | | | | |
|---|---|---|---|---|
| 9,744,344 | B1 * | 8/2017 | Devgon | ............ A61M 39/0247 |
| 9,750,446 | B2 * | 9/2017 | Devgon | ................ A61B 5/154 |
| 10,064,576 | B2 | 9/2018 | Devgon | |
| 10,076,272 | B2 * | 9/2018 | Devgon | ............ A61B 5/15003 |
| 10,143,411 | B2 | 12/2018 | Cabot | |
| 10,300,247 | B2 | 5/2019 | Devgon et al. | |
| 2014/0094774 | A1 * | 4/2014 | Blanchard | ........ A61M 25/0105 |
| | | | | 604/164.08 |
| 2014/0364766 | A1 * | 12/2014 | Devgon | ........... A61B 5/150221 |
| | | | | 600/581 |
| 2017/0216564 | A1 * | 8/2017 | Devgon | ............ A61M 25/0113 |
| 2019/0209812 | A1 | 7/2019 | Burkholz et al. | |
| 2019/0321590 | A1 * | 10/2019 | Burkholz | ........ A61M 25/09041 |
| 2020/0016374 | A1 | 1/2020 | Burkholz et al. | |
| 2020/0297382 | A1 * | 9/2020 | Coppedge | ......... A61B 17/3472 |

FOREIGN PATENT DOCUMENTS

| | | |
|---|---|---|
| CN | 110693578 A | 1/2020 |
| CN | 215916113 U | 3/2022 |
| JP | 2017532985 A | 11/2017 |
| JP | 2019509781 A | 4/2019 |
| WO | 2016033143 A1 | 3/2016 |
| WO | 2019203997 A2 | 10/2019 |

* cited by examiner

VASCULAR ACCESS DEVICE AND RELATED SYSTEMS AND METHODS

RELATED APPLICATIONS

This application claims the benefit of U.S. Provisional Patent Application No. 62/993,685, filed on Mar. 23, 2020, entitled "VASCULAR ACCESS DEVICE AND RELATED SYSTEMS AND METHODS," which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient to obtain a blood sample.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

Blood withdrawal or infusion using the catheter may be difficult for several reasons, particularly when a dwelling time of the catheter within the patient is more than one day. For example, when the catheter is left inserted in the patient for a prolonged period of time, the catheter may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is desired, an additional needle stick is used to provide vein access for blood collection, which may be painful for the patient and result in higher material costs.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a vascular access device that may house an instrument such as, for example, a guidewire, a probe, or an intravenous catheter, as well as related systems and methods. In some embodiments, the vascular access device may deliver the instrument through an existing peripheral intervascular catheter for blood collection, fluid delivery, patient or device monitoring, or other clinical needs. In some embodiments, the instrument may be introduced into the catheter to overcome complications that can prevent fluid flow, such as thrombus or fibrin sheath buildup at the catheter tip, valves, vein collapse, or other obstructions. The instrument may push past such occlusions to clear a pathway for fluid flow into or out of the vein.

In some embodiments, the vascular access device may include a housing comprising a proximal end, a distal end, a slot, and an advancement tab. The advancement tab may be configured to move linearly along the slot between a retracted position and an advanced position. The instrument may be disposed within the housing and thereby protected from damage or contamination from the external environment. In some embodiments, the distal end of the housing may include a fluid seal disposed within the distal end of the housing. The fluid seal may maintain a closed fluid path.

A proximal end of the instrument may be coupled to the advancement tab. In response to the advancement tab moving from the retracted position to the advanced position, the distal tip of the instrument may be advanced beyond the distal end of the housing.

In some embodiments, the housing may be substantially rigid. In some embodiments, the distal end of the housing may comprise a coupler element, such as a luer adapter, to couple to a catheter assembly. In other embodiments, the coupler element may comprise a cannula and multiple lever lock arms to couple to a catheter assembly. Some embodiments may include a lock element disposed within the housing to prevent disengagement of the catheter assembly from the housing. The lock element may be actuated in response to the advancement tab moving in a distal direction beyond the retracted position. In some embodiments, the lock element may include a biasing element or cam element to automatically lock the coupler element in response to the advancement tab being moved in a distal direction beyond the retracted position.

In some embodiments, such as where the coupler element includes the cannula and the plurality of lever lock arms, the lock element may be disposed between the housing and the plurality of lever lock arms in response to the instrument being in the advanced position. This may prevent depression of the plurality of lever lock arms and thus prevent release of the catheter assembly from the housing. In response to the instrument being in the retracted position, the lock element may be disposed proximal to the lever lock arms, thereby enabling the lever lock arms to depress and thus release the catheter assembly from the housing.

In some embodiments, the vascular access device may include a T-adapter or a Y-adapter coupled to the distal end of the housing to couple to the catheter assembly. In some embodiments, an extension tube may extend from the T-adapter or the Y-adapter and a blood collection pathway may extend through the extension tube and used to obtain a blood sample. The instrument may be a guidewire.

In some embodiments, the extension tube may extend from the housing between the distal end of the housing and a distal end of the slot. In other embodiments, the extension tube may extend from the housing between the proximal end of the housing and a proximal end of the slot. A blood collection pathway may extend through the extension tube and may be used to obtain a blood sample.

In some embodiments, the vascular access device may include a stop feature to automatically maintain a position of the advancement tab relative to the slot. In some embodiments, the stop feature may be coupled to the advancement tab and may interact with a feature of the housing. The stop feature may thus obstruct linear movement of the instrument between the retracted position and the advanced position. In other embodiments, the stop feature may be coupled to the housing and interact with the advancement tab to obstruct linear movement of the instrument.

In some embodiments, a method for providing vascular access may include coupling the vascular access device to the catheter assembly. The catheter assembly may include a catheter adapter including a proximal end, a distal end, and a catheter extending from the distal end. The vascular access device may include a housing comprising a proximal end, a distal end, and a slot. An advancement tab may be configured to move linearly along the slot between a retracted position and an advanced position.

In some embodiments, an instrument may be disposed within the housing. The instrument may include a proximal end and a distal tip. The proximal end of the instrument may be coupled to the advancement tab. In response to movement of the advancement tab from the retracted position to the advanced position, the distal tip of the instrument may be advanced beyond the distal end of the housing.

In some embodiments, coupling the vascular access device to the catheter assembly may include coupling the housing to the catheter assembly. In some embodiments, the method may further include moving the advancement tab linearly along the slot from the retracted position to the advanced position. In response to the advancement tab moving to the advanced position, the distal tip of the instrument may extend beyond the distal end of the housing.

In some embodiments, the method may further include actuating a lock element to secure the vascular access device to the catheter assembly. The lock element may be actuated in response to the advancement tab moving in a distal direction beyond the retracted position. In some embodiments, a position of the advancement tab may be automatically maintained relative to the slot. In some embodiments, a force to the advancement tab may be applied to release the position.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION

As used in this specification, the term "distal" refers to a direction away from a clinician who would place the device into contact with a patient, and nearer to the patient. The term "proximal" refers to a direction nearer to the clinician who would place the device into contact with the patient, and farther away from the patient. Thus, for example, the end of a catheter first touching the body of the patient is the distal end, while the opposite end of the catheter is the proximal end of the catheter.

Figures 1A, 1B:
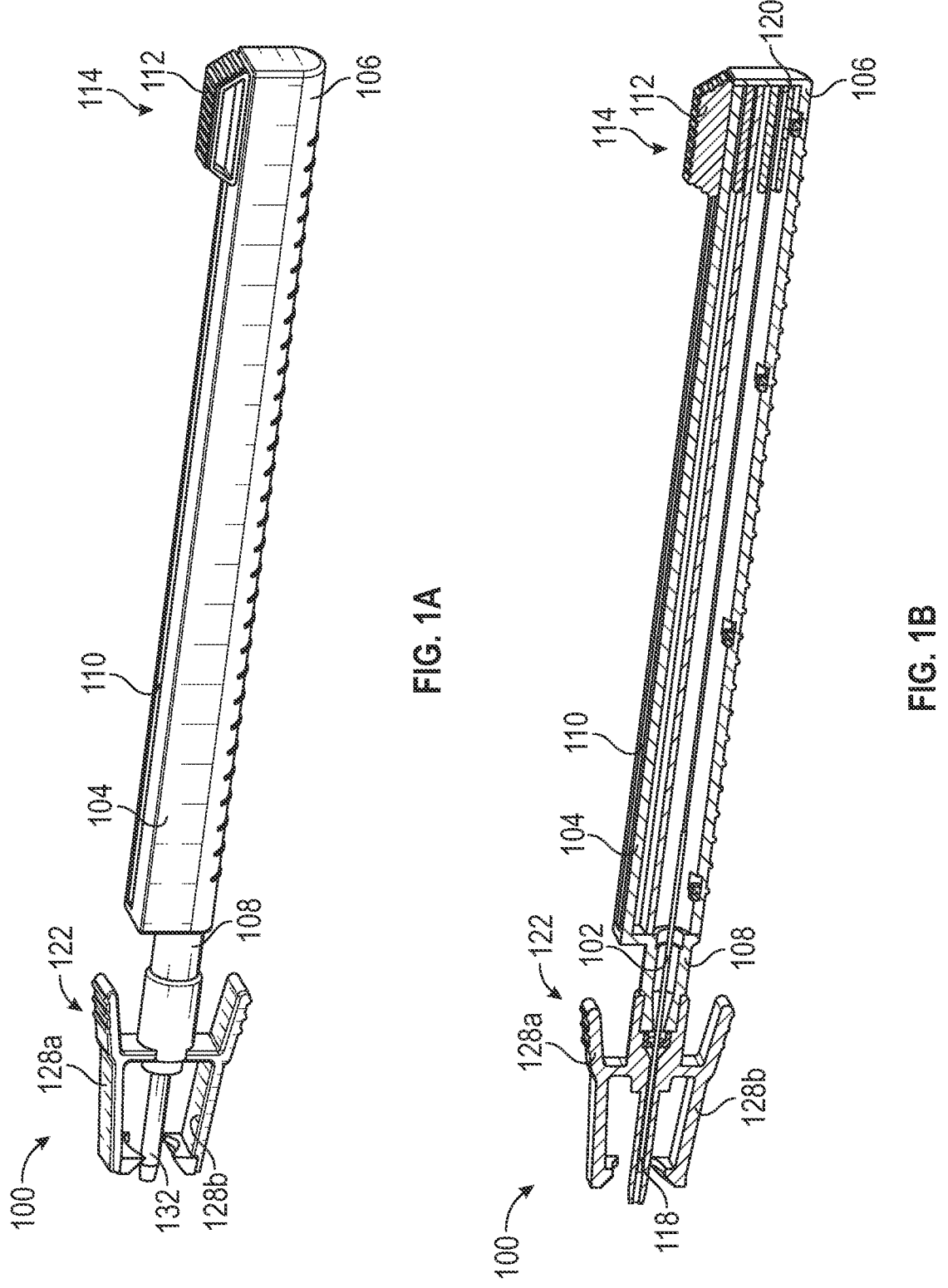
FIG. 1A is an upper perspective view of an example vascular access device, illustrating an example instrument in a retracted position according to some embodiments.
FIG. 1B is a cross-sectional view of the vascular access device of FIG. 1A.
Figures 20, 21:
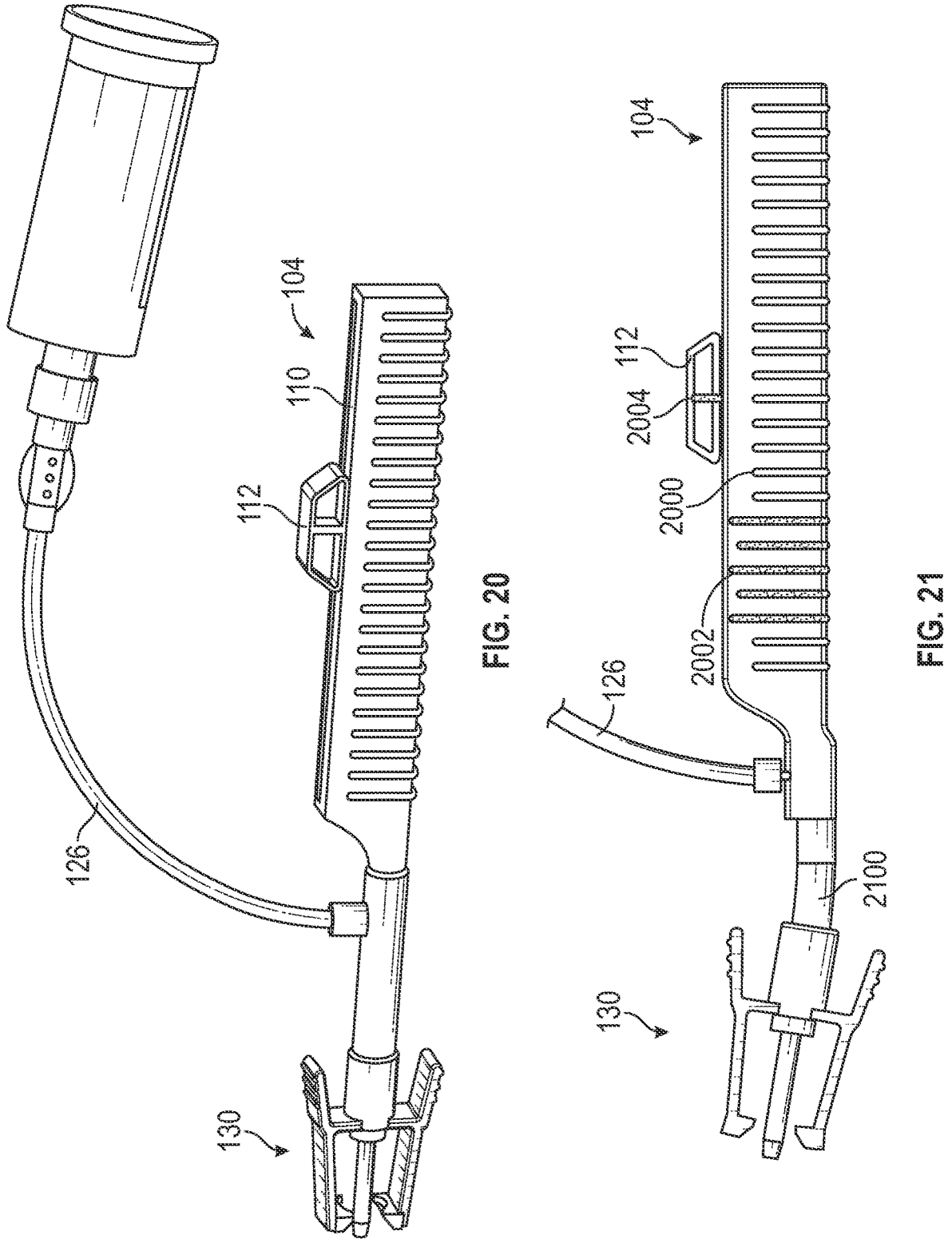
FIG. 20 is a perspective view of an example housing attached to a blood draw adapter in accordance with some embodiments.
FIG. 21 is a perspective view of an example vascular access device having a flexible joint in accordance with some embodiments.

Referring now to FIGS. 1A and 1B, in some embodiments, a vascular access device 100 may be configured to deliver an instrument 102 through a catheter of a catheter assembly for blood collection, fluid delivery, patient or device monitoring, or other clinical needs, for example. An example catheter assembly is illustrated in FIG. 21. In some embodiments, the catheter may include a peripheral IV catheter, a peripherally-inserted central catheter, or a midline catheter. In some embodiments, the catheter through which the instrument 102 is delivered may have been previously inserted into the vasculature of the patient and may be dwelling within the vasculature.

In some embodiments, the instrument 102 may be advanced through a fluid pathway of the catheter and the catheter assembly such that a distal tip 118 of the instrument 102 is placed into the vasculature of the patient distal to a distal tip of the catheter. In some embodiments, in operation, a clinician may deploy the instrument 102 to push past any occlusions in the catheter or vasculature (e.g., thrombus or fibrin buildup at the catheter tip, vein collapse, valves, etc.) to create a clear pathway for fluid flow.

In some embodiments, the instrument 102 may be disposed within a housing 104 configured to protect the instrument 102 from damage and/or contamination from a surrounding external environment. In some embodiments, the housing may be rigid or semi-rigid. In some embodiments, the housing 104 may be made of one or more of stainless steel, aluminum, polycarbonate, metal, ceramic, plastic, and another suitable material. In some embodiments, the housing 104 may include a proximal end 106, a distal end 108, a slot 110, and an advancement tab 112. In some embodiments, the slot 110 may extend parallel to a longitudinal axis of the housing 104. In some embodiments, as discussed in more detail below, the distal end 108 of the housing 104 may be coupled to a coupler element 122, such as a luer connector, to connect to the catheter assembly, for example.

In some embodiments, the instrument 102 may include, for example, a guidewire, another catheter, a probe, or another suitable instrument. In some embodiments, the instrument 102 may include various openings and/or sensors. In some embodiments, the instrument 102 may include elements of both a probe and a catheter. In some embodiments, the openings and/or sensors may be disposed towards the distal tip 118 of the instrument 102. In some embodiments, the openings may serve as fluid inlets and/or outlets. In some embodiments, the sensors may measure one or more parameters and/or detect one or more elements related to, for example, diagnostic information, blood chemistry, pressure, flow rate, drug identification, microbes, placement of an implantable stent, in-vein catheter tip stabilization feature, or other device, etc.

In some embodiments, the advancement tab 112 may be configured to move linearly along the slot 110 between a retracted position 114 and an advanced position 116. In some embodiments, the advancement tab 112 may be coupled to a proximal end 120 of the instrument 102, such that moving the advancement tab 112 linearly along the slot 110 may cause the instrument 102 to move in a same direction as the advancement tab 112 relative to the housing 104. In some embodiments, a clinician may pinch or grasp the advancement tab 112 to move the instrument 102 between the retracted position 114 and the advanced position 116. As described in more detail below, in some embodiments, a distance traveled by the instrument 102 relative to the housing 104 may be proportional to a distance traveled by the advancement tab 112 relative to the slot 110, and may include any ratio.

Figures 2A, 2B:
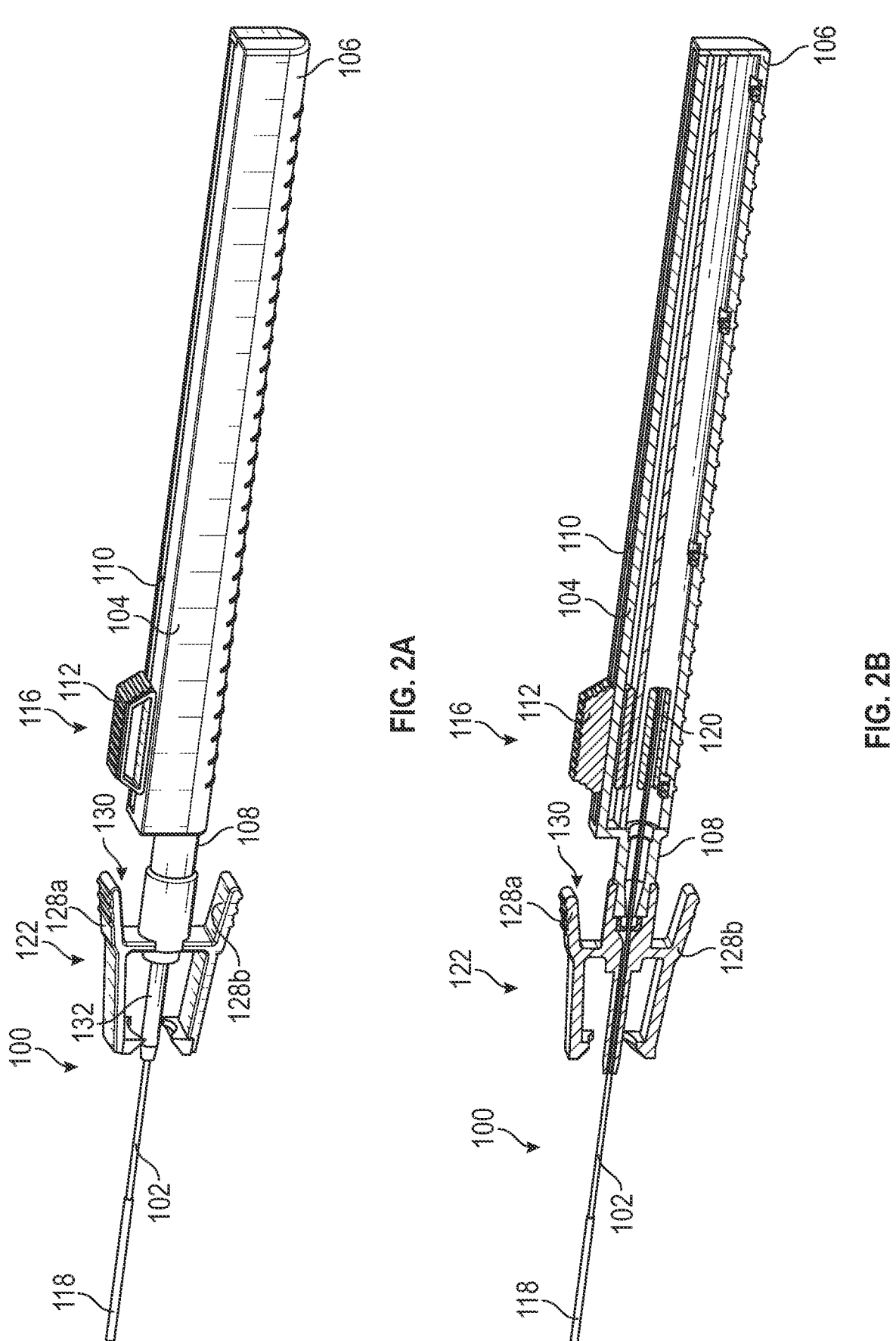
FIG. 2A is an upper perspective view of the vascular access device of FIG. 1A, illustrating the instrument in an advanced position according to some embodiments.
FIG. 2B is a cross-sectional view of the vascular access device of FIG. 1A, illustrating the instrument in the advanced position according to some embodiments.

In some embodiments, as illustrated in FIGS. 2A and 2B, movement of the advancement tab 112 from the retracted position 114 to the advanced position 116 may cause a distal tip 118 of the instrument 102 to be advanced beyond the distal end 108 of the housing 104. In some embodiments, moving the advancement tab 112 to the advanced position 116 may introduce the instrument 102 into the catheter assembly, for example. In some embodiments, in response to the instrument 102 being introduced into the catheter assembly, the instrument 102 may access a fluid pathway of the catheter assembly and/or the vasculature of a patient.

In some embodiments, the catheter of the catheter assembly with significant dwelling time within the vasculature may be susceptible to narrowing, collapse, kinking, blockage by debris (e.g., fibrin or platelet clots), and adhering of a tip of the catheter to the vasculature. Thus, blood withdrawal using the catheter may be difficult. In some embodiments, the instrument 102 may include a guidewire or another catheter having a diameter less than a diameter of the catheter of the catheter assembly to provide access to the vasculature of the patient without any additional needle sticks. In some embodiments, the guidewire may clear the pathway for collecting a blood sample. Thus, in some embodiments, the vascular access device 100 may be used for needle-free blood collection and/or fluid infusion.

In some embodiments, the advancement tab 112 may be moved along the slot 110 from the advanced position 116 to the retracted position 114 to withdraw or retract at least a portion of the instrument 102 into the housing 104.

Figure 3:
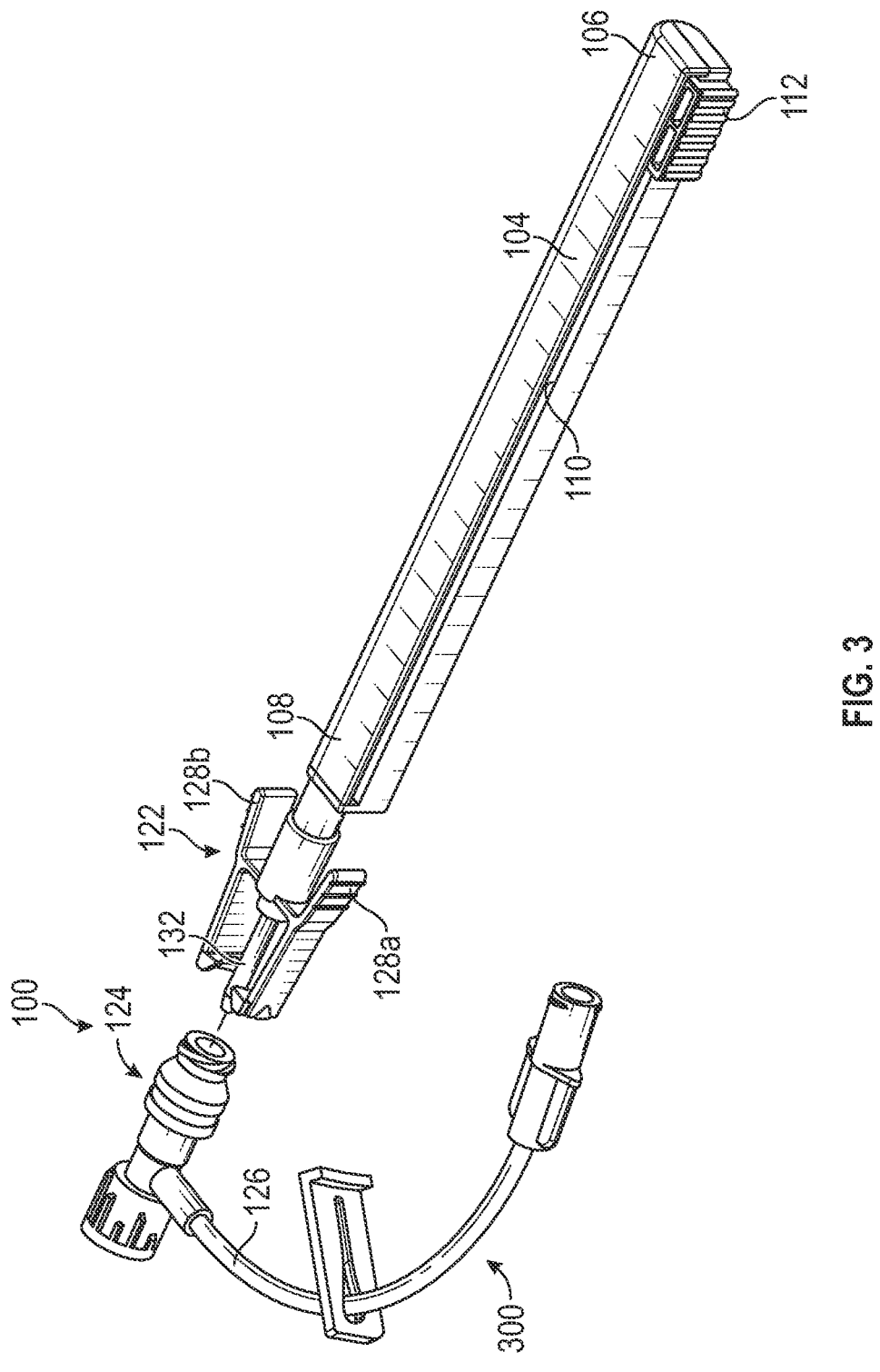
FIG. 3 is a partial exploded view of the vascular access device and an example adapter according to some embodiments.
Figure 4:
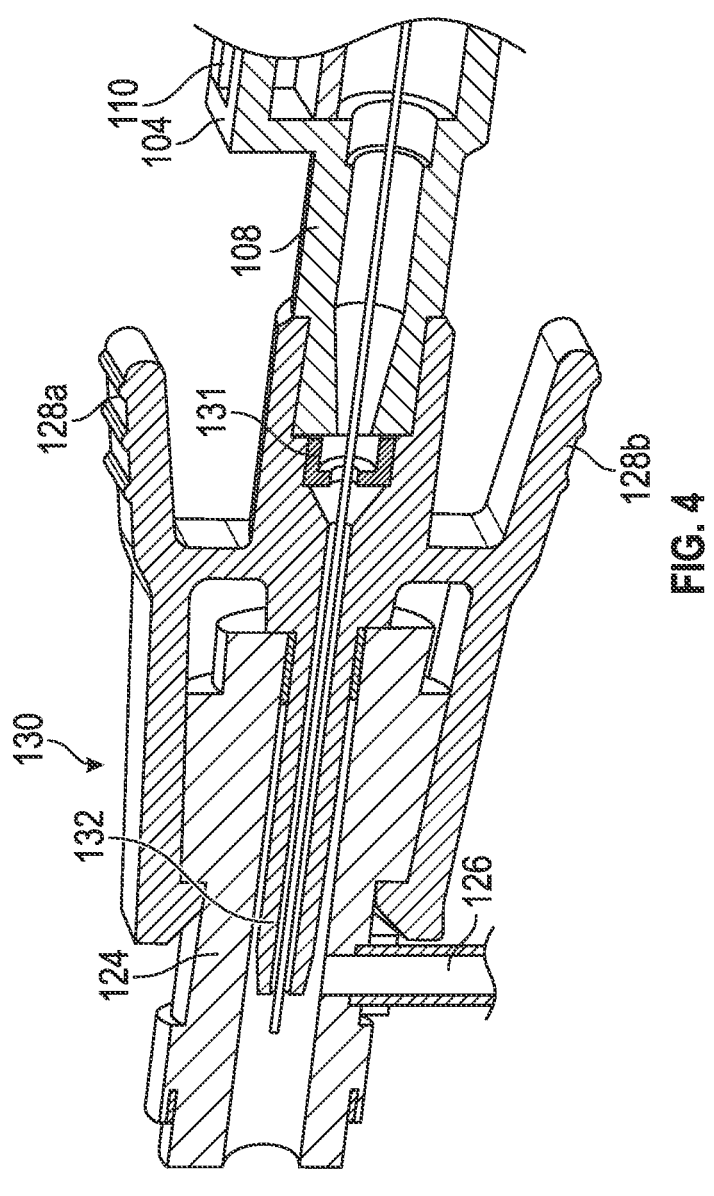
FIG. 4 is a cross-sectional view of the vascular access device and the adapter of FIG. 3.
Figure 5:
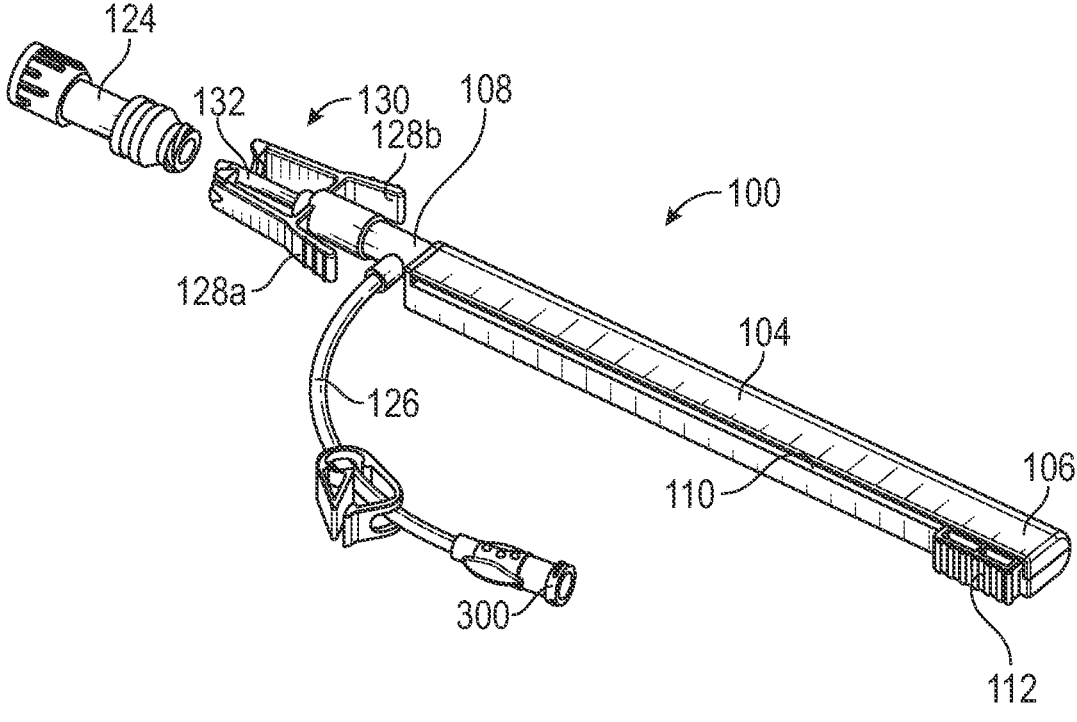
FIG. 5 is an exploded view of another example vascular access device according to some embodiments.
Figure 6:
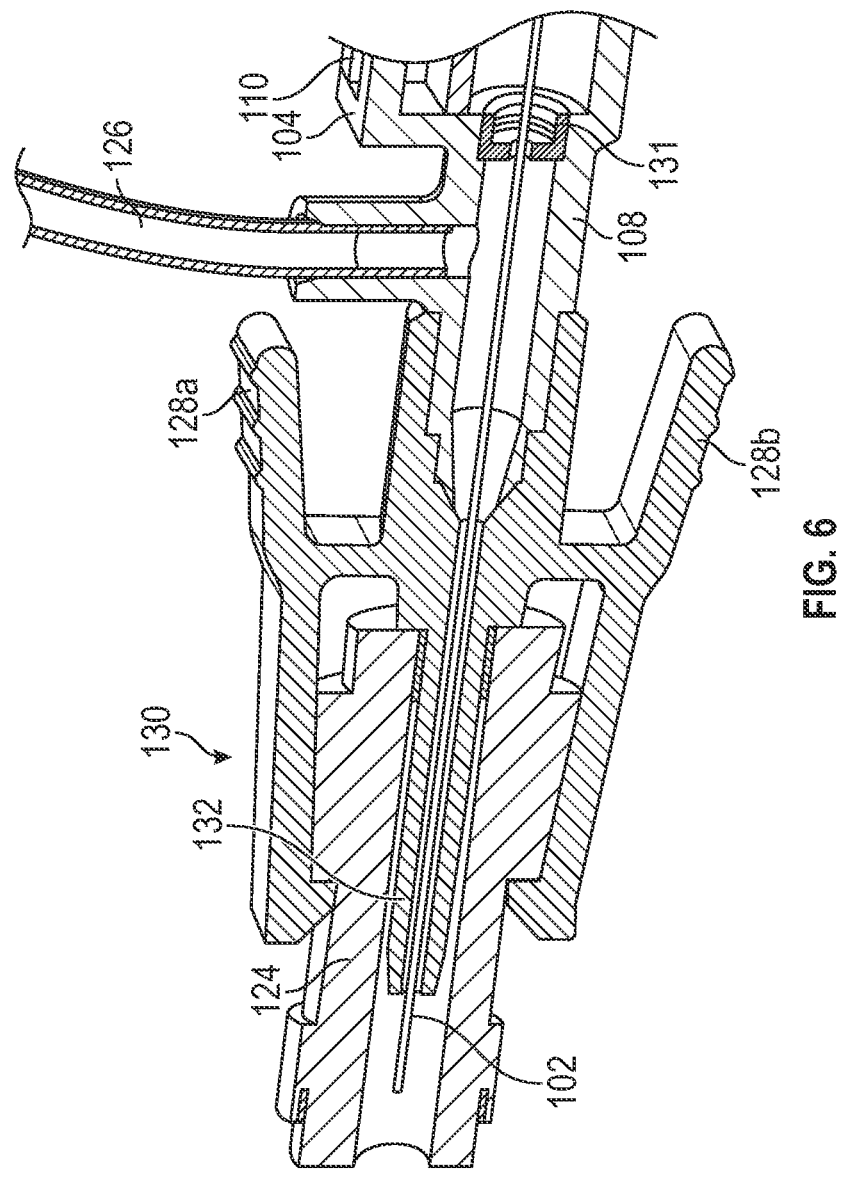
FIG. 6 is a cross-sectional view of the vascular access device of FIG. 5 and another example adapter according to some embodiments.

Referring now to FIGS. 3-8, in some embodiments, an extension tube 126 may be coupled to the vascular access device 100, and the extension tube 126 may be used for blood collection and/or fluid infusion. may be infused into or withdrawn from a patient's vein may be oriented in any of various ways. As illustrated in FIG. 5-6, in some embodiments, the extension tube 126 may extend directly from the housing 104. In some embodiments, the coupler element 122 may include a lever lock 130, for example. In some embodiments, the coupler element 122 may include a luer connector, such as a male or female luer connector. In some embodiments, the extension tube 126 may extend from the housing 104 between the distal end 108 of the housing 104 or the lever lock 130 and a distal end of the slot 110.

As illustrated in these and other embodiments, a fluid seal 131 may be disposed at or within the distal end 108 of the housing 104 to enable the instrument 102 to advance and/or retract from the distal end 108 while maintaining a closed fluid path. In other embodiments, such as, for example, where the extension tube 126 extends from the proximal end 106 of the housing 104, the fluid seal 131 may be disposed at or within the proximal end 106 of the housing 104 to permit movement of the instrument 102 therethrough while maintaining a closed fluid path. In some embodiments, the fluid seal 131 may include silicone, rubber, an elastomer, or another suitable material. In some embodiments, the fluid seal 131 may include an aperture, slit, or the like to accommodate the instrument 102 therethrough.

As illustrated in FIG. 3-4, in some embodiments it may be advantageous to direct a fluid pathway of a vascular access system through an adapter 124, such as a T-adapter or a Y-adapter, coupled to the housing 104. In some embodiments, the extension tube 126 may extend from the adapter 124 such that the fluid pathway, such as a blood collection pathway, may be directed through the extension tube 126 rather than through the housing 104. In these and other embodiments, such as where the fluid pathway is used to obtain a blood sample, for example, an internal diameter and length of the extension tube 126 may be selected to balance shear stress over a length of the fluid pathway, thereby reducing blood hemolysis.

Figures 7, 8:
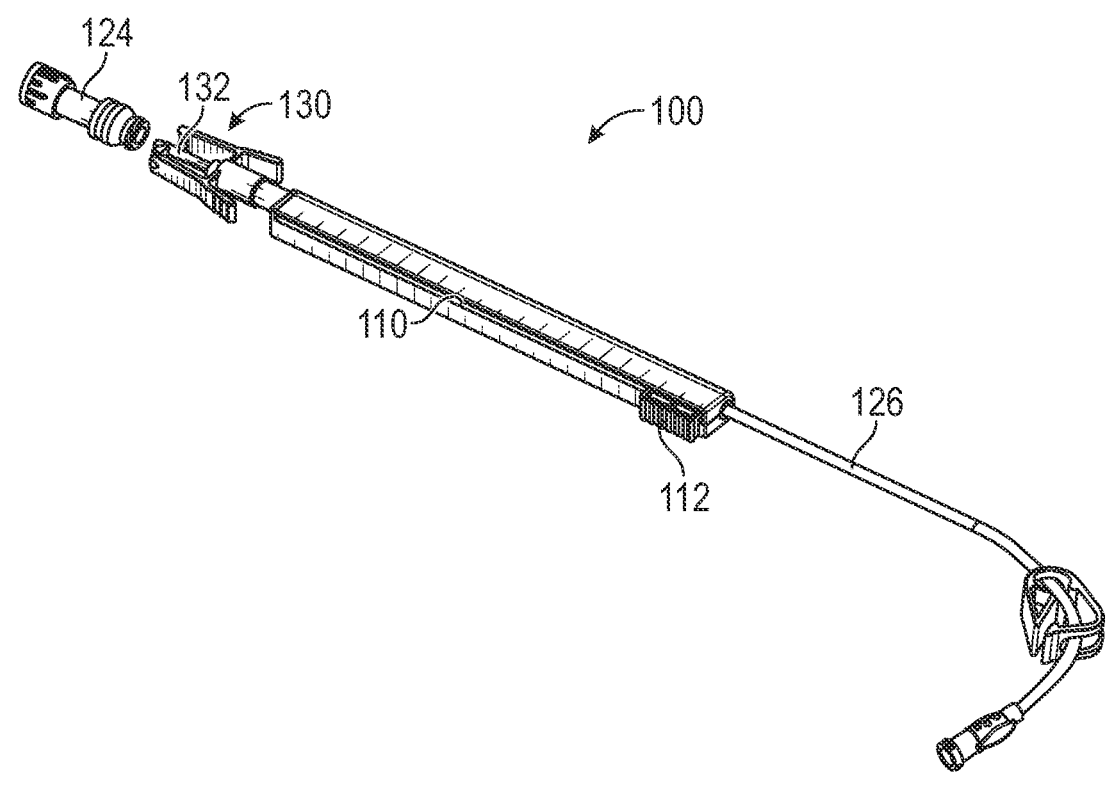
FIG. 7 is an upper perspective view of another example vascular access device illustrating a fluid pathway extending from a proximal end of the housing according to some embodiments.
FIG. 8 is a cross-sectional view of the vascular access device of FIG. 7 and another an example adapter according to some embodiments.
Figures 9A, 9B:
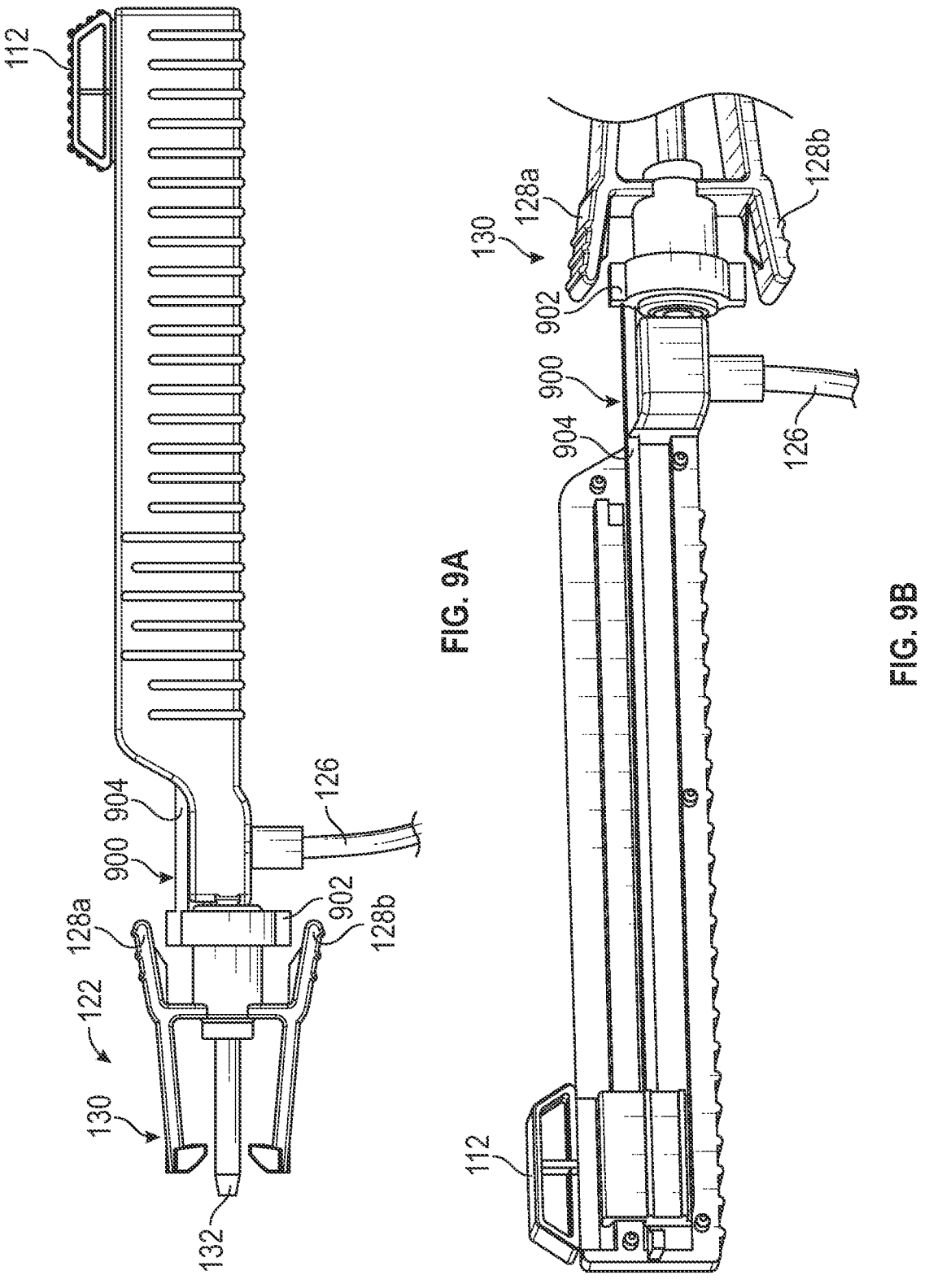
FIG. 9A is an upper perspective view of an example housing including a lock element in an unlocked position in accordance with some embodiments.
FIG. 9B is a cross-sectional view of the housing and the lock element of FIG. 9A.
Figures 10A, 10B:
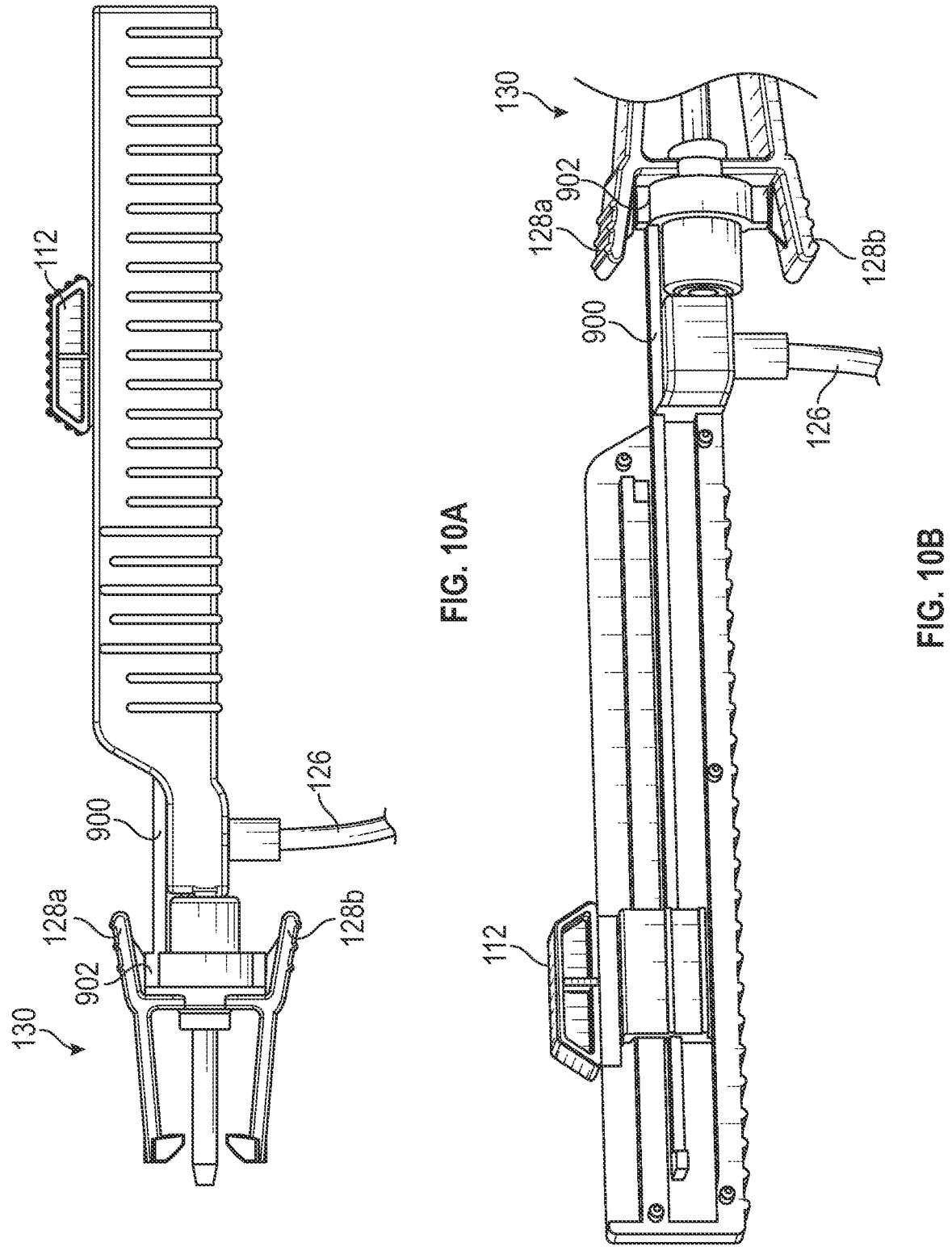
FIG. 10A is an upper perspective view of another example housing including a lock element in a locked position in accordance with some embodiments.
FIG. 10B is a cross-sectional view of the housing and lock element of FIG. 10A.

As illustrated in FIGS. 7-8, in some embodiments, the extension tube 126 may extend from the proximal end 106 of the housing 104. In some embodiments, the extension tube 126 may extend from the housing 104 from the proximal end 106 of the housing 104 proximal to a proximal end of the slot 110. In some embodiments, a proximal end of the extension tube 126 may include a connector 300, which may include a luer connector or another suitable connector, coupled thereto.

In some embodiments, the connector 300 may be coupled to a blood collection device, such as, for example, a VACU-TAINER® or a VACUTAINER® LUER-LOK™, available from Becton Dickinson and Company of Franklin Lakes, New Jersey. In some embodiments, the connector 300 may be coupled to an infusion device. In some embodiments, the fluid pathway of the vascular access system may extend through the catheter assembly and/or the adapter 124. In some embodiments, the fluid pathway of the vascular access system may extend through all or a portion of the housing 104.

In some embodiments, a length L of the extension tube 126 may be selected based on one or more of the following: a gauge of a particular catheter, a particular catheter assembly configuration, or a clinical setup. In some embodiments, the extension tube 126 may include an inner diameter D.

Fluid flow in a fluid pathway through the extension tube 126 that is tubular can be analyzed using Poiseuille's equation:

$$Q = \frac{\pi D^4 \Delta P}{128 \mu L} = \frac{\Delta P}{R_f}$$

where ΔP is a change in pressure gradient across the length of the fluid pathway, D and L are the inner diameter and length, respectively, of the fluid pathway, μ is the viscosity of a fluid, and $$R_f = \frac{128 \mu L}{\pi D^4}$$

8 is the fluid resistance. Since μ is the viscosity of the fluid and not part of the extension tube geometry, a geometric factor $G_f$ is defined such that $R_f$ (the fluid resistance) is $$R_f = \frac{128\mu}{\pi}$$

$G_f$, where $$G_f = \frac{L}{D^4}.$$

In some embodiments, the extension tube 126 may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the extension tube 126 may have an inner diameter that changes over the length of the extension tube 126, the geometric factor is then:

$$G_f = \int_0^L \frac{dl}{D(l)^4}$$

In some embodiments, the extension tube 126 may have a cross section that is not circular or may have a complicated inner diameter profile. The geometric factor can then be determined by measuring the flow rate (Q) at given pressure (ΔP) with known viscosity (μ) fluid:

$$G_f = \frac{\pi \Delta P}{128 \mu Q}$$

The $G_f$ value of the extension tube 126 may be selected to reduce the maximum shear stress for each catheter gauge to be the same or less than the max shear stress of a BD 21G VACUTAINER® UltraTouch™ push button blood collection set (available from Becton, Dickinson & Company of Franklin Lakes, New Jersey), which was previously considered the gold standard for blood draws. In some embodiments, $G_f$ value of the extension tube 126 may be selected to reduce the maximum shear stress for each catheter gauge to be the same or less than the max shear stress of a BD 25G VACUTAINER® UltraTouch™ push button blood collection set (available from Becton, Dickinson & Company of Franklin Lakes, New Jersey).

In some embodiments, the fluid pathway of the vascular access system, which may include one or more of the blood collection device, the extension tube 126, the adapter 124, and the catheter assembly, may include an entirety of a blood collection pathway through which blood flows after leaving the vasculature and into or through the blood collection device during blood collection. The system geometric factor $G_{fs}$ for the fluid pathway of the vascular access system can be determined in similar fashion as the $G_f$ value of the extension tube 126 described earlier. In some embodiments, the system geometric factor $G_{fs}$ with the instrument 102 at the advanced position may be equal to or more than 7.34E+

06 (1/in$^3$). In some embodiments, $G_{f_s}$ may include another value. In some embodiments, the system geometric factor $G_{f_s}$ with the instrument 102 at the advanced position may be 7.34E+06 (1/in$^3$) plus or minus 10 percent, plus or minus 25 percent, plus or minus 50 percent, or plus or minus 75 percent. In some embodiments, $G_{f_s}$ may include another value, which may be selected based on a gauge and/or length of the catheter.

In some embodiments, the instrument 102 disposed in the housing 104 may be maintained in a non-fluid environment and protected from contamination and environmental hazards until use. Advantageously, in some embodiments, the extension tube 126 may also allow maintenance of a closed system and aseptic technique, while reducing disturbance or dislodgement of the catheter and/or a catheter securement dressing.

In some embodiments, the distal end 108 of the housing 104 may include the lever lock 130 to couple the housing 104 to the catheter assembly. The lever lock 130 may include a cannula 132 and at least two of the lever lock arms 128a, b. In some embodiments, the cannula 132 may be blunt. In some embodiments, the cannula 132 may extend from the distal end 108 of the housing 104 in a direction substantially aligned with a longitudinal axis of the housing 104. In some embodiments, the lever lock arms 128a, b may be spaced apart from each other, and in some embodiments, may be situated substantially opposite each other relative to the cannula 132.

In some embodiments, in operation, the cannula 132 may penetrate a luer connector of the catheter assembly to access the fluid pathway of the catheter assembly. In some embodiments, proximal ends of the lever lock arms 128a, b may be biased inwardly towards the longitudinal axis of the housing 104 to snap to or otherwise couple to the luer connector. In this manner, the lever lock arms 128a, b may automatically secure the cannula 132 to the luer connector. In some embodiments, the luer connector of the catheter assembly may include one or more recesses configured to receive one or more protrusions of the lever lock arms 128a, b. In some embodiments, the lever lock arms 128a, b may engage the protrusions of the lever lock arms 128a, b to secure the housing 104 to the catheter assembly.

Figure 15A:
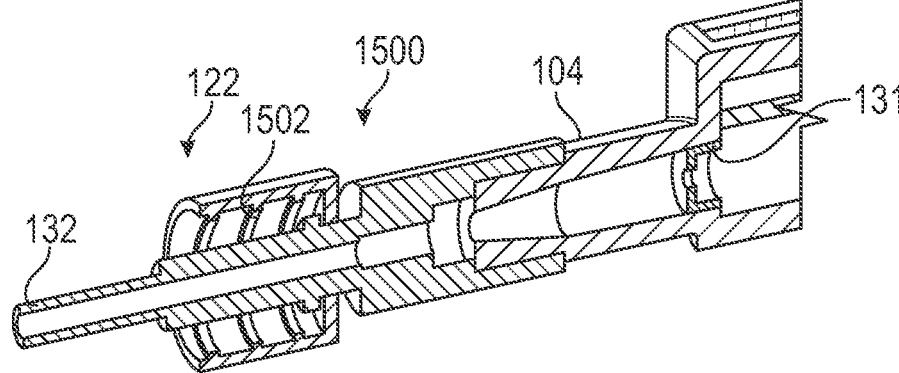
FIG. 15A is a cross-sectional view of an example luer adapter in accordance with some embodiments.
Figure 15B:
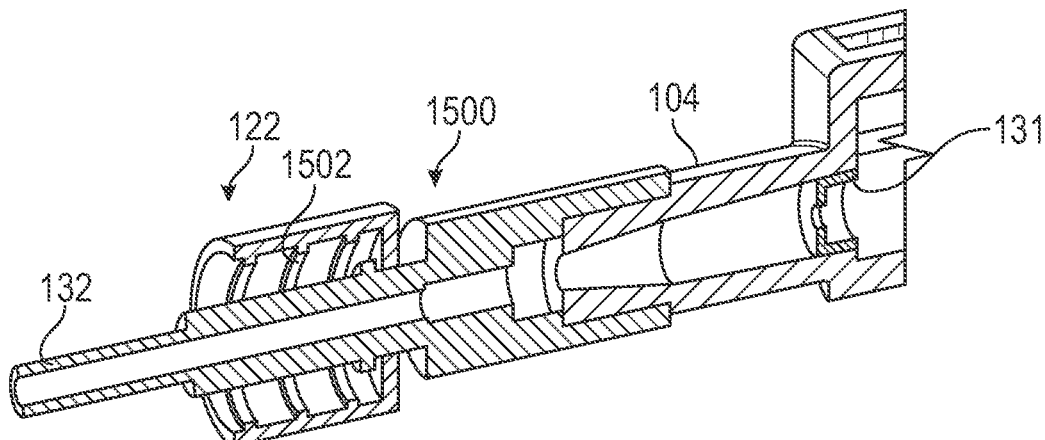
FIG. 15B is a cross-sectional view of another example luer adapter in accordance with some embodiments.
Figure 15C:
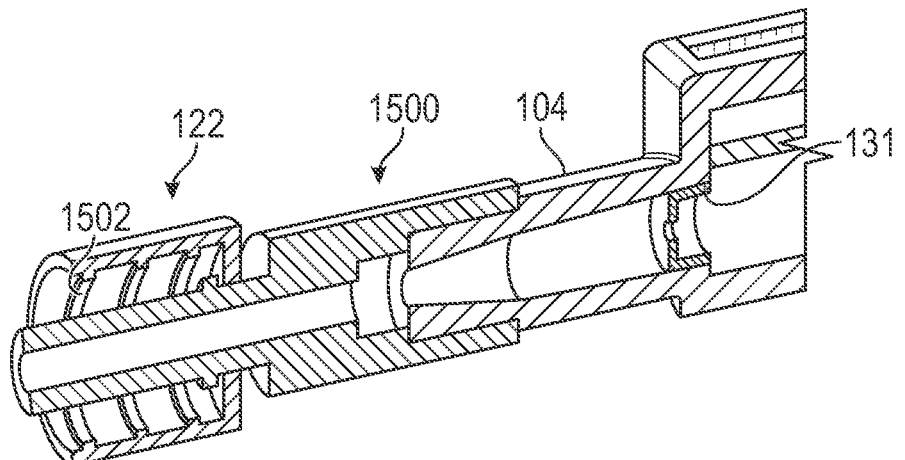
FIG. 15C is a cross-sectional view of another example luer adapter in accordance with some embodiments.

Referring now to FIGS. 15A-15C, in some embodiments, the coupler element 122 may include a luer connector, such as, for example, a male luer connector, to connect to the catheter assembly. In some embodiments, the luer connector may include a luer lock connector 1500, which may include internal threads 1502 to engage corresponding threads of a luer connector of the catheter assembly. In some embodiments, the luer lock connector 1500 may further include a cannula 132 to penetrate or insert into the luer connector of the catheter assembly.

In some embodiments, the coupler element 122, such as the lever lock 130 (see, for example, FIGS. 1-11) or luer lock connector 1500, may be fixed to the housing 104. In other embodiments, the coupler element 122 may be coupled to the housing 104 and configured to rotate to any clock position with respect thereto.

Figure 16A:
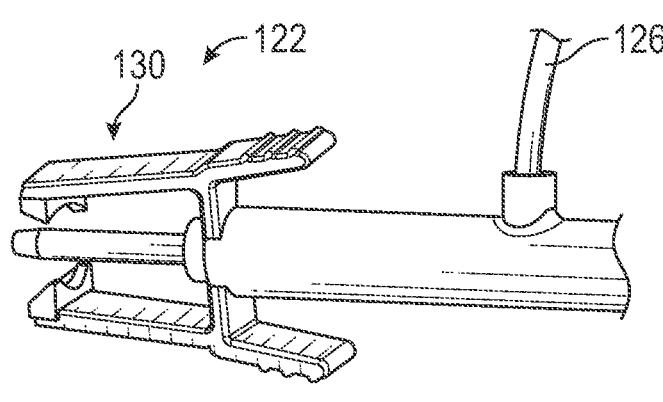
FIG. 16A is a perspective view of an example lever lock containing an extension tube in accordance with some embodiments.
Figure 16B:
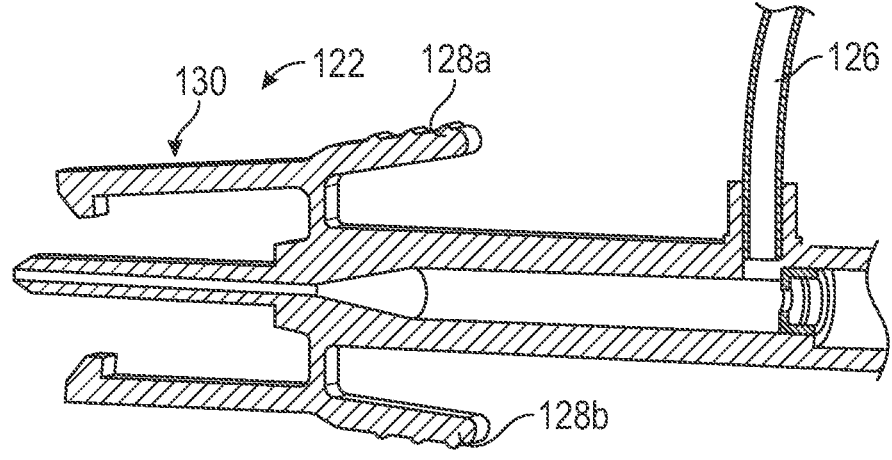
FIG. 16B is a cross-sectional view of the lever lock of FIG. 16A.

Referring to FIGS. 16A and 16B, in some embodiments, the coupler element 122, such as the lever lock 130 (see, for example, FIGS. 1-11) or luer lock connector 1500 (see, for example, FIG. 15), the coupler element 122 may be monolithically formed with the housing 104 as a single unit.

Referring now to FIGS. 9A-B and 10A-B, some embodiments may include a lock element 900 to selectively or automatically secure the housing 104 to the catheter assembly while the instrument 102 is advanced into the catheter.

In some embodiments, as discussed above, the coupler element 122 may include the cannula 132 and the lever lock arms 128a, b to couple to a catheter assembly. In these and other embodiments, the lock element 900 may include a locking member 902 configured to interact with the lever lock arms 128a, b. The locking member 902 may be integrated with or coupled to an elongated extension member 904 disposed within the housing 104 and extending along a length or portion of the length thereof.

In some embodiments, in response to the instrument 102 being in the advanced position 116, the locking member 902 may be disposed in a locked position between the housing 104 and the lever lock arms 128a, b. In this position, the locking member 902 may prevent depression of the lever lock arms 128a, b and thus prevent release of the catheter assembly from the housing 104. In response to the instrument 102 being in the retracted position 114, the locking member 902 may be disposed proximal to the lever lock arms 128a, b in an unlocked position, thereby enabling the lever lock arms 128a, b to depress and to thus release the catheter assembly from the housing 104.

In some embodiments, the lock element 900 may include a biasing element, such as a spring, or a cam element, such as a cam and follower, disposed within the housing 104 and automatically actuated in response to the advancement tab 112 moving in a distal direction beyond the retracted position 114. The biasing element or cam element may automatically activate the lock element 900 to lock the coupler element 122 and thereby prevent disengagement of the catheter assembly from the housing 104.

Specifically, in some embodiments, the elongated extension member 904 may be held proximal such that the locking member 902 is in an unlocked position when the advancement tab 112 is in the retracted position 114. Upon the advancement tab 112 being moved distally to advance the instrument 102 into the catheter, the locking member 902 may be released. The biasing element or cam element may then push the locking member 902 in a distal direction to engage the lever lock arms 128a, b in the locked position.

Similarly, when the advancement tab 112 is actuated to retract the instrument 102, a final movement in a proximal direction may pull the locking member 902 against the biasing element or cam element, thus unlocking the lever lock arms 128a, b. This may prevent a user from removing the instrument 102 from the catheter assembly when the advancement tab 112 is in any position except its most proximal and retracted position 114.

Of course, as one skilled in the art will recognize, the automatic locking mechanism may be reversed such that the biasing member or cam element pulls the locking member 902 to disengage the lock and pushes the locking member 902 into engagement to secure the catheter assembly to the housing 104. In some embodiments, the automatic locking mechanism may be activated when movement of the advancement tab 112 begins or ends. In some embodiments, the locking member 902 may rotate in and out of a locked position rather than sliding forward and backward.

Figures 12, 13, 14:
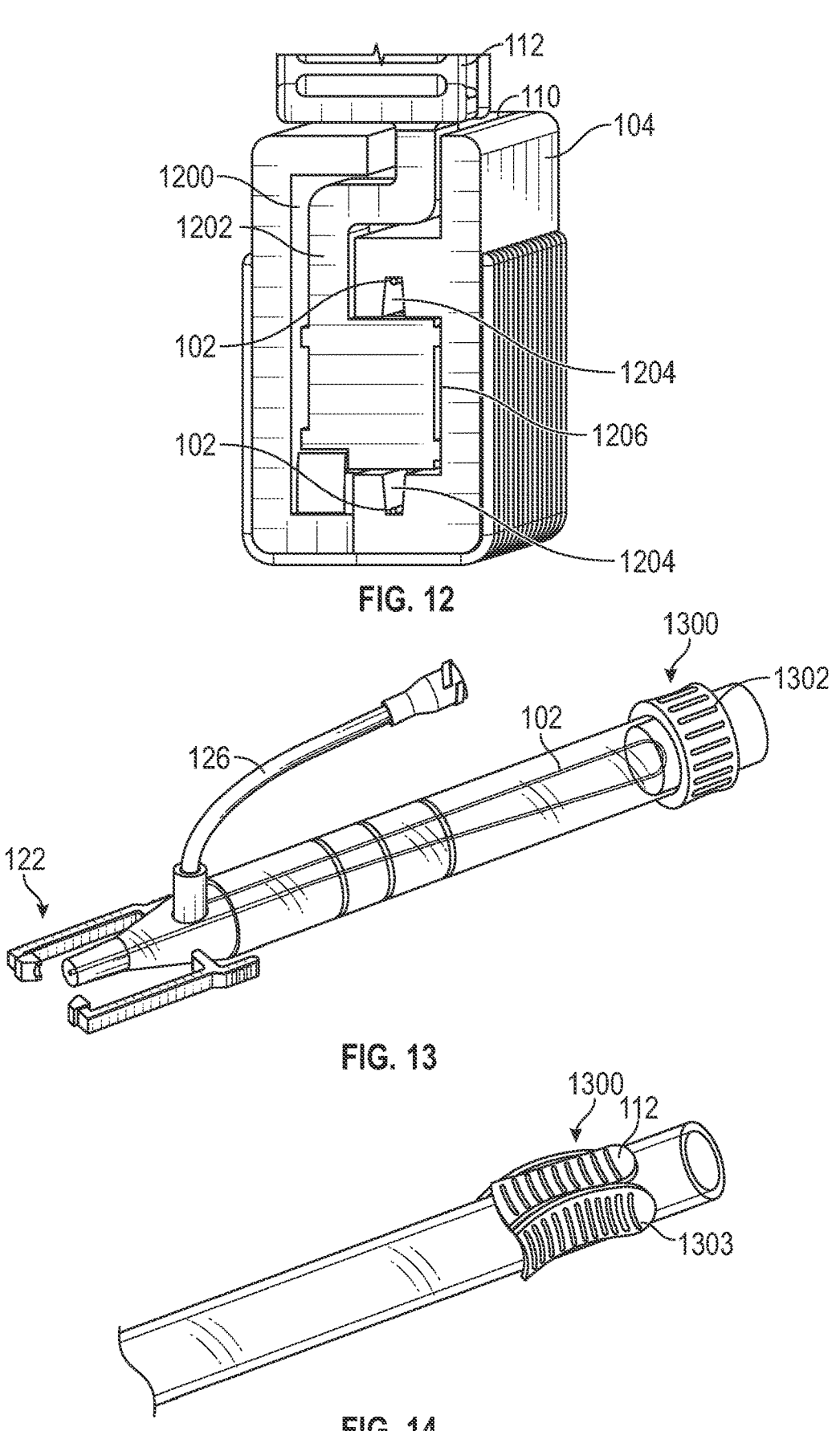
FIG. 12 is a cross-sectional view of an example housing including a guide element according to some embodiments.
FIG. 13 is a cross-sectional view of an example vascular access device configured for single-handed operation in accordance with some embodiments.
FIG. 14 is an upper perspective view of an example advancement tab configured for single-handed operation in accordance with some embodiments.
Figure 17:
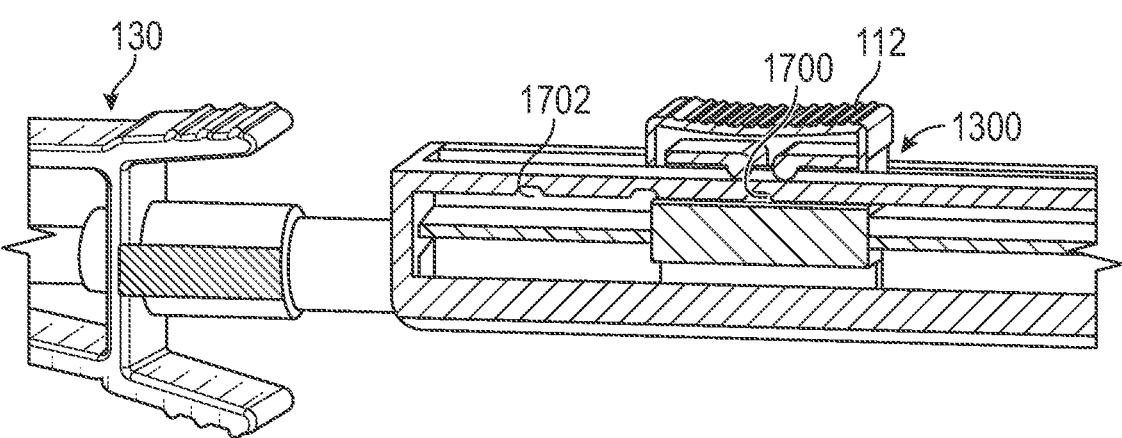
FIG. 17 is a cross-sectional view of one example of an advancement tab and stop feature in accordance with some embodiments.

Referring now to FIGS. 13, 14, and 17, in some embodiments, a position of the advancement tab 112 may be controlled before, during and after use of the instrument 102. In some embodiments, the vascular access device 100 may include a stop feature 1300 to automatically maintain a position of the advancement tab 112 relative to the slot 110. In some embodiments, the stop feature 1300 may be coupled to the advancement tab 112 and may interact with a feature of the housing 104. The stop feature 1300 may thus obstruct linear movement of the instrument 102 between the retracted position 114 and the advanced position 116. In other embodiments, the stop feature 1300 may be coupled to the housing 104 and interact with the advancement tab 112 to obstruct linear movement of the instrument 102.

In some embodiments, the stop feature 1300 may provide engineered friction between the advancement tab 112 and the housing 104 such that movement of the advancement tab 112 requires an application of force. Absent such application of force, the advancement tab 112 may maintain its linear position along the slot 110. In some embodiments, the stop feature 1300 may apply friction along an entire length of the slot 110.

In some embodiments, the stop feature 1300 may comprise simple interference between the advancement tab 112 and the housing 104, and may use the modulus of the material of the advancement tab 112 as a spring for control. For example, in some embodiments, both the advancement tab 112 and the housing 104 may have substantially elliptical cross-sections. The advancement tab 112 may be configured to rotate with respect to the housing 104 to thereby lock a position of the advancement tab 112.

In some embodiments, the stop feature 1300 may be a cantilever integral to the advancement tab 112 or housing 104 that acts as a spring. In other embodiments, the stop feature 1300 may include a separate spring member attached to the advancement tab 112 to apply friction as the advancement tab 112 slides against the housing 104, or vice versa. In some embodiments, the surface finish and/or materials used for the advancement tab 112 and/or housing 104, in addition to the spring force, may be selected to optimize friction between the two.

In some embodiments, the stop feature 1300 may substantially correspond to the distal and/or proximal ends 108, 106 of the slot 110 or housing 104, thus corresponding to the advanced and/or the retracted position 116, 114 of the instrument 102. In some embodiments, the stop feature 1300 may include one or more detents or other features integrated with or coupled to the distal and/or proximal ends 108, 106 of the slot 110 or housing 104. In some embodiments, the detents may interact mechanically or magnetically with the advancement tab 112 to hold the advancement tab 112 at the advanced and/or retracted positions 116, 114. In this manner, the instrument 102 may be maintained in a fully retracted or fully inserted position. Of course, one or more detents may be implemented at any position along the slot 110 or housing 104 to maintain the advancement tab 112 at any such position. In some embodiments, one or more detents may be implemented in addition to another stop feature 1300.

Referring now to FIG. 17, in some embodiments, the stop feature 1300 may include a spring-loaded catch 1700 integrated with or coupled to the advancement tab 112. The spring-loaded catch 1700 may automatically engage a recess 1702 disposed in the housing 104 as the advancement tab 112 travels linearly along the slot 110. The advancement tab 112 may be selectively depressed to release the spring-loaded catch 1700 from the recess 1702. Releasing the spring-loaded catch 1700 in this manner may allow the advancement tab 112 to slide in a linear direction along the slot 110 to advance or remove the instrument 102. In some embodiments, the recess 1702 may be integrated in the housing 104 at any desired position or distance along the slot 110 or housing 104.

Figure 11:
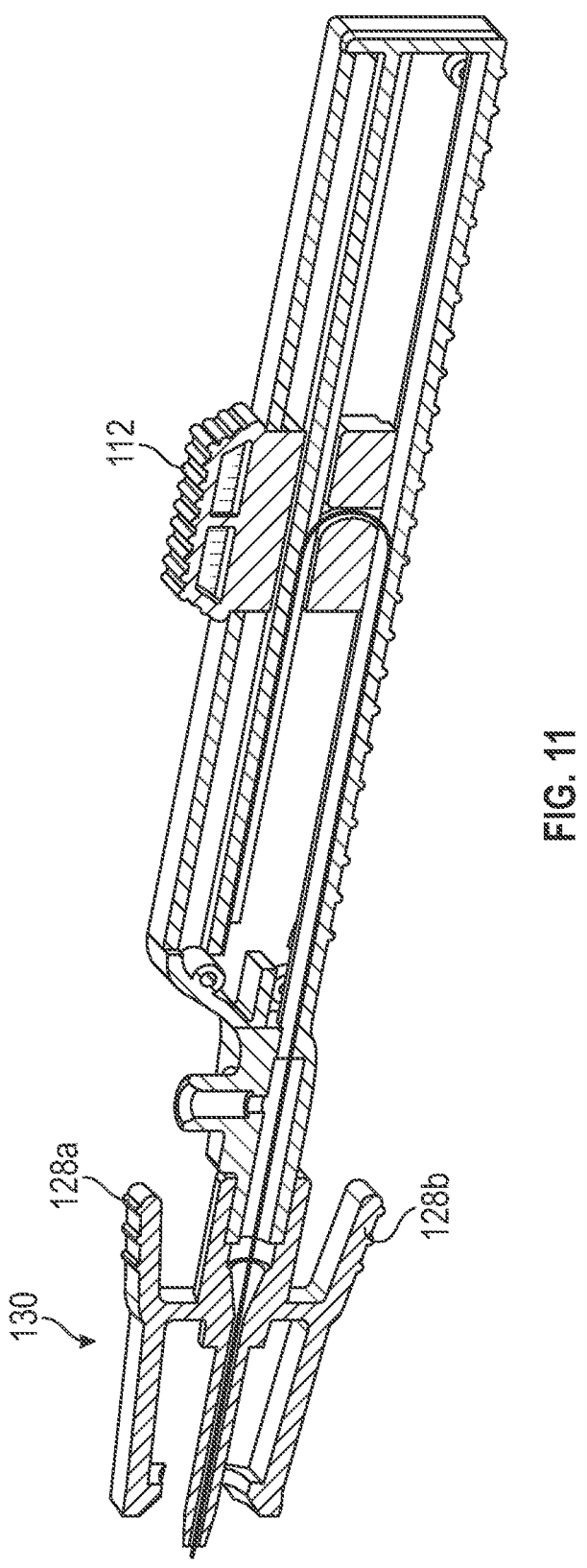
FIG. 11 is a cross-sectional view of an example housing configured to advance an instrument twice the distance traveled by the advancement tab according to some embodiments.
Figures 18, 19:
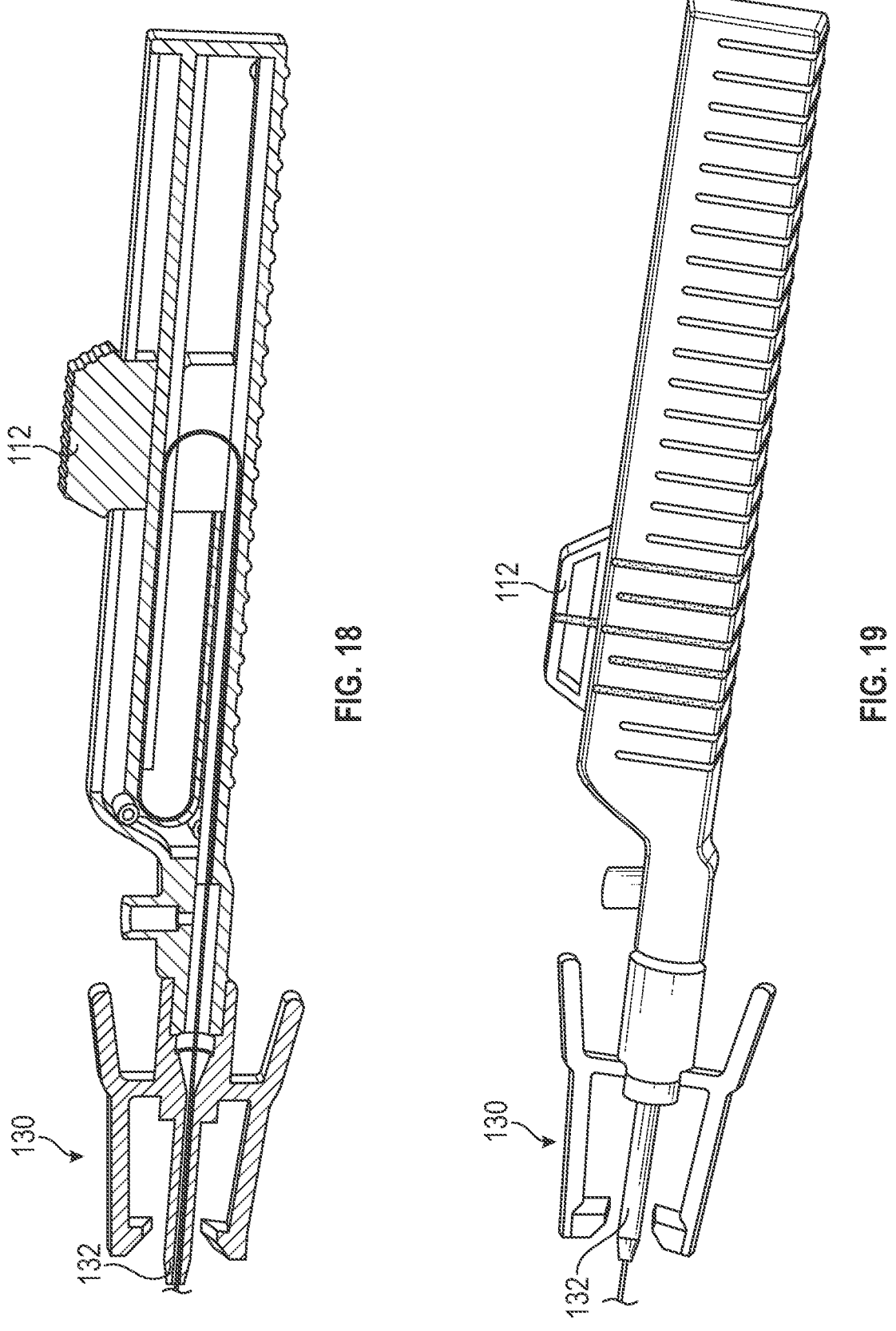
FIG. 18 is a cross-sectional view of an example vascular access device configured to advance an instrument three times the distance traveled by the advancement tab in accordance with some embodiments.
FIG. 19 is an upper perspective view of the vascular access device of FIG. 18.

Referring now to FIGS. 11 and 18-19, in some embodiments, the advancement tab 112 may be configured to advance the instrument 102 farther than the advancement tab 112 itself travels. As illustrated in FIG. 11, for example, the advancement tab 112 may be configured to advance the instrument 102 greater than, such as twice, the distance traveled by the advancement tab 112 by attaching a proximal end 120 of the instrument 102 to the distal end 108 of the housing 104, facing the proximal direction. In some embodiments, the instrument 102 may make a "U" turn through the advancement tab 112 and exit the housing 104 at the distal end 108. In some embodiments, the advancement tab 112 may push on the "U" portion of the instrument 102 to advance the instrument 102 and may pull on the "U" portion of the instrument 102 to retract the instrument 102. The instrument 102 may slide through the advancement tab 112 as it moves. In this manner, the advancement tab 112 may act as a pulley to move the instrument 102 a distance twice that traveled by the advancement tab 112.

Referring now to FIG. 18-19, in some embodiments, one or more additional bends may be incorporated into the instrument 102 prior to attaching the proximal end 120 to the advancement tab 112. This may enable the advancement tab 112 to further increase the distance traveled by the instrument 102 relative to the distance traveled by the advancement tab 112 by a factor equal to the number of bends or "U" turns. In some embodiments, the factor may equal the number of bends or "U" turns in the instrument 102 plus one. For example, no bends may correspond to 1$x$ advancement between the instrument 102 and the advancement tab 112, 1 bend may correspond to 2$x$ advancement between the instrument 102 and the advancement tab 112, 2 bends may correspond to 3$x$ advancement between the instrument 102 and the advancement tab 112, etc. Configuring the instrument 102 and advancement tab 112 in this manner, however, may cause the instrument 102 to buckle during insertion. Accordingly, some embodiments may include guides or constraints to support the instrument 102 to prevent buckling.

For example, referring to FIG. 12, some embodiments my include a guide element 1204 disposed in the housing 104 to constrain the instrument 102. In some embodiments, the guide element 1204 may be disposed within a bore 1206 of the housing 104 containing the instrument 102. In some embodiments, the guide element 1204 may be coupled to the advancement tab 112 via a connector member 1202. In some embodiments, the connector member 1202 may be configured to substantially occupy a tortuous path 1200 between the bore 1206 and the slot 110. The connector member 1202 may thereby occlude the tortuous path 1200 and prevent contamination that might otherwise enter the slot 110 and reach the instrument 102. In other embodiments, the connector member 1202 may occupy a direct path between the slot 110 and the bore 1206 and/or instrument 102.

In some embodiments, such as where the advancement tab 112 moves the instrument 102 a distance twice that traveled by the advancement tab 112 for example, the guide element 1204 may occupy a space between the portions of the instrument 102 forming the "U" shape. In this manner, the instrument 102 may be constrained on three sides, thereby preventing movement of the instrument 102 in those three directions. To prevent buckling in the fourth direction, some embodiments may include a shield element to selectively shield the open area in the fourth direction. In some embodiments, the shield element may be selectively removed to advance the instrument 102 therethrough. In other embodiments, the instrument 102 may include a small bend or bias to cause the instrument 102 to tend away from the open area or side, and instead into a wall or constrained area.

Advantageously, configuring the advancement tab 112 to advance the instrument 102 farther than distance traveled by the advancement tab 112 may facilitate a housing 104 that is compact, having reduced dimensions and a reduced slot 110 length. In other words, the distance that the advancement tab 112 must travel to advance and retract the instrument 102 may be reduced, thus requiring a vascular access device 100 having a more compact design. The vascular access device 100 may be operated with just one hand as a result.

Indeed, as illustrated in FIGS. 13 and 14, some embodiments of the vascular access device 100 may be operated by moving a single finger or thumb while holding the vascular access device 100 in the same hand. Some embodiments of the vascular access device 100 allowing for single-handed operation may include a collar advancement grip 1302 or a central grip 1303. As illustrated, the collar advancement grip 1302 or the central grip 1303 may allow single-handed advancement of the advancement tab 112 with the clinician or user holding the housing 104 with thumb and middle finger. The collar advancement grip 1302 or the central grip 1303 may be translated with an index finger, for example.

Referring now to FIGS. 20-21, in some embodiments, the housing 104 may include one or more markings 2000 or measurements, which may visually indicate to a clinician or other user an insertion depth of the instrument 102. In some embodiments, the markings 2000 may be a scale 2002 on a side of the housing 104 that may align with an indicator 2004 on the advancement tab 112. In some embodiments, the scale 2002 may be fixed for use with a specific catheter setup and length. In some embodiments, the markings 2000 may include a table to indicate the position for different catheter setups and lengths. In some embodiments, the scale 2002 may be a sliding scale 2002 and/or indicator 2004 that can be adjusted depending on catheter setup and length.

In some embodiments, the markings 2000 may indicate how far to insert and/or withdraw one or more different instruments 102 such as different types of catheters, for example. In some embodiments, the markings 2000 may indicate one or more of the following: the advanced position 116 of the instrument 102, the retracted position 114 of the instrument 102, and various positions between the advanced position 116 and the retracted position 114 of the instrument 102. Some embodiments may include an icon to indicate alignment between the catheter tip and the distal tip 118 of the instrument 102. In some embodiments, additional icons may indicate specific distances beyond the catheter tip traveled by the distal tip 118 of the instrument 102.

In some embodiments, the distance between the markings 2000 may be adjusted in the event the vascular access device 100 includes an instrument 102 and advancement tab 112 configuration that has a multiplier effect on the distance traveled by the instrument 102 relative to the advancement tab 112. Of course, the multiplier may be any number or ratio known to those in the art.

Referring now to FIG. 20, in some embodiments a blood draw adapter 2006 may be fixed to the vascular access device 100. For example, in some embodiments, the blood draw adapter 2006 may be directly bonded to the extension tube 126. In other embodiments, the blood draw adapter 2006 or may be coupled to the vascular access device 100 via a luer connection, for example, to allow the blood draw adapter 2006 to be selectively removed and replaced with another device, such as a syringe.

Referring now to FIG. 21, in some embodiments, a flexible joint 2100 may be incorporated between the lever lock 130 or other coupler element 122 and the housing 104. The flexible joint 2100 may provide flexibility between attachment to the catheter and the housing 104. In some embodiments, the flexible joint 2100 may include a short piece of tubing or a ball and socket coupled to the housing 104 and/or lever lock 130 or other coupler element 122.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A vascular access device, comprising:
a housing, comprising a proximal end, a distal end, a slot, and an advancement tab configured to move linearly along the slot between a retracted position and an advanced position;
a coupler element at the distal end of the housing comprising a cannula and at least one-lever lock arm configured to couple to a catheter assembly;
a lock element coupled to the housing configured to prevent depression of the at least one lever lock arm to prevent disengagement of the at least one lever lock arm from the catheter assembly; and
an instrument disposed within the housing, the instrument comprising a proximal end and a distal tip, wherein the proximal end of the instrument is coupled to the advancement tab, wherein in response to movement of the advancement tab from the retracted position to the advanced position, the distal tip of the instrument is advanced beyond the distal end of the housing;
wherein the lock element is operably connected to the advancement tab, with movement of the advancement tab to the advanced position causing a corresponding distal movement of the lock element to a position that prevents depression of the at least one lever lock arm.

2. The vascular access device of claim 1, wherein the instrument comprises a guidewire, a catheter, or a probe.

3. The vascular access device of claim 1, wherein the housing is substantially rigid.

4. The vascular access device of claim 1, wherein the lock element is disposed within the housing to prevent disengagement of the catheter assembly in response to the advancement tab being moved in a distal direction beyond the retracted position.

5. The vascular access device of claim 1, further comprising:
a T-adapter or a Y-adapter coupled to the distal end of the housing; and
an extension tube extending from the T-adapter or the Y-adapter, wherein a blood collection pathway extends through the extension tube, and wherein the instrument comprises a guidewire.

6. The vascular access device of claim 1, further comprising an extension tube extending from the housing between the distal end of the housing and a distal end of the slot, wherein a blood collection pathway extends through the extension tube, and wherein the instrument comprises a guidewire.

7. The vascular access device of claim 1, further comprising an extension tube extending from the housing between the proximal end of the housing and a proximal end of the slot, wherein a blood collection pathway extends through the extension tube, and wherein the instrument comprises a guidewire.

8. The vascular access device of claim 1, further comprising a stop feature to automatically maintain a position of the advancement tab relative to the slot.

9. The vascular access device of claim 8, wherein the stop feature is coupled to the advancement tab and interacts with a feature of the housing to obstruct linear movement of the instrument between the retracted position and the advanced position.

10. The vascular access device of claim 8, wherein the stop feature is coupled to the housing and interacts with the advancement tab to obstruct linear movement of the instrument between the retracted position and the advanced position.

11. The vascular access device of claim 1, further comprising a fluid seal disposed within the distal end of the housing to maintain a closed fluid path.

12. The vascular access device of claim 1, wherein the locking element includes an elongated extension member movably disposed within the housing and extending along a length thereof.

13. The vascular access device of claim 1, wherein the locking element includes a locking member movable from (i) a locked position between the housing and the at least one lever lock arm to prevent depression of the at least one lever lock arm, to (ii) an unlocked position proximal to the at least one lever lock arm to permit depression of the at least one lever lock arm.

14. A vascular access device, comprising:

a housing, comprising a proximal end, a distal end, a slot, and an advancement tab configured to move linearly along the slot between a retracted position and an advanced position, wherein the distal end of the housing comprises a coupler element to couple to a catheter assembly;

an instrument disposed within the housing, the instrument comprising a proximal end and a distal tip, wherein the proximal end of the instrument is coupled to the advancement tab, wherein in response to movement of the advancement tab from the retracted position to the advanced position, the distal tip of the instrument is advanced beyond the distal end of the housing; and a lock element disposed within the housing to lock the coupler element to prevent disengagement of the catheter assembly from the housing in response to the advancement tab being moved in a distal direction beyond the retracted position, wherein the lock element comprises a biasing element or a cam element to automatically lock the coupler element in response to the advancement tab being moved in a distal direction beyond the retracted position.

15. A vascular access device, comprising:

a housing, comprising a proximal end, a distal end, a slot, and an advancement tab configured to move linearly along the slot between a retracted position and an advanced position, wherein the distal end of the housing comprises a coupler element to couple to a catheter assembly;

an instrument disposed within the housing, the instrument comprising a proximal end and a distal tip, wherein the proximal end of the instrument is coupled to the advancement tab, wherein in response to movement of the advancement tab from the retracted position to the advanced position, the distal tip of the instrument is advanced beyond the distal end of the housing; and a lock element disposed within the housing to lock the coupler element to prevent disengagement of the catheter assembly from the housing in response to the advancement tab being moved in a distal direction beyond the retracted position, wherein the coupler element comprises a cannula and a plurality of lever lock arms configured to couple to a catheter assembly, and wherein in response to the instrument being in the advanced position, the lock element is disposed between the housing and the plurality of lever lock arms to prevent depression of the plurality of lever lock arms to release the catheter assembly from the housing.

16. A method, comprising:

coupling a vascular access device to a catheter assembly, the catheter assembly comprising a catheter adapter including a proximal end, a distal end, and a catheter extending from the distal end, wherein the vascular access device comprises:

a housing, comprising a proximal end, a distal end, a slot, and an advancement tab configured to move linearly along the slot between a retracted position and an advanced position; and an instrument disposed within the housing, the instrument comprising a proximal end and a distal tip, wherein the proximal end of the instrument is coupled to the advancement tab, wherein in response to movement of the advancement tab from the retracted position to the advanced position, the distal tip of the instrument is advanced beyond the distal end of the housing;

wherein coupling the vascular access device to the catheter assembly comprises coupling the housing to the catheter assembly with at least one lever lock arm;

actuating a lock element to move from (i) an unlocked position proximal to the at least one lever lock arm that permits depression of the at least one lever lock arm towards the housing, to (ii) a locked position between the housing and the at least one lever lock arm to prevent depression of the at least one lever lock arm towards the housing to prevent disengagement of the at least one lever lock arm from the catheter assembly; and moving the advancement tab linearly along the slot from the retracted position to the advanced position, wherein in response to the advancement tab moving to the advanced position, the distal tip of the instrument extends beyond the distal end of the housing;

wherein actuating the lock element is in response to the advancement tab moving in a distal direction beyond the retracted position.

17. The method of claim 16, wherein moving the advancement tab comprises automatically maintaining a position of the advancement tab relative to the slot.

18. The method of claim 17, wherein moving the advancement tab comprises applying a force to the advancement tab to release the position.

* * * * *